United States Patent [19]

Bushroe

[11] Patent Number: 5,164,994
[45] Date of Patent: Nov. 17, 1992

[54] SOLDER JOINT LOCATOR

[75] Inventor: Michael W. Bushroe, Marana, Ariz.

[73] Assignee: Hughes Aircraft Company, Los Angeles, Calif.

[21] Appl. No.: 454,804

[22] Filed: Dec. 21, 1989

[51] Int. Cl.$^5$ ............................................. G06K 9/00
[52] U.S. Cl. ...................................... 382/8; 382/25; 378/58
[58] Field of Search ............... 382/8, 25, 28; 356/237; 378/58

[56] References Cited

U.S. PATENT DOCUMENTS

| | | | |
|---|---|---|---|
| 4,103,287 | 7/1978 | Frank | 382/22 |
| 4,183,013 | 1/1980 | Agrawala et al. | 382/26 |
| 4,189,711 | 2/1980 | Frank | 382/22 |
| 4,445,137 | 4/1984 | Panofsky | 358/101 |
| 4,499,597 | 2/1985 | Alves | 382/27 |
| 4,748,676 | 5/1988 | Miyagawa et al. | 382/28 |
| 4,790,023 | 12/1988 | Matsui et al. | 382/25 |
| 4,791,676 | 12/1988 | Flickner et al. | 382/22 |
| 4,809,308 | 2/1989 | Adams et al. | 378/58 |
| 4,852,131 | 7/1989 | Armistead | 378/58 |
| 4,894,790 | 1/1990 | Yotsuga et al. | 382/8 |
| 4,910,757 | 3/1990 | Kiyasu et al. | 378/58 |
| 4,926,452 | 5/1990 | Baker et al. | 382/8 |
| 4,955,062 | 9/1990 | Terui | 382/8 |

*Primary Examiner*—David K. Moore
*Assistant Examiner*—Barry Stellrecht
*Attorney, Agent, or Firm*—R. M. Heald; C. D. Brown; W. K. Denson-Low

[57] ABSTRACT

A system (82) and method for locating features in an image. In the preferred embodiments, the present invention accepts as input a tilted view X-ray image of a PC board (10), as well as expected locations of solder joints (18) in the PC board (10). The present invention then determines the actual center locations (32) of these solder joints (18) by defining windows within the image and checking individual areas within the window, to see if they fall below a predetermined threshold. In addition, the system (82) determines if these pixels are connected to other pixels that have been previously determined to be part of the solder joint (18). Finally, the system (82) determines the center of the group of pixels determined to be part of the solder joint and displays the coordinate location of this center.

16 Claims, 5 Drawing Sheets

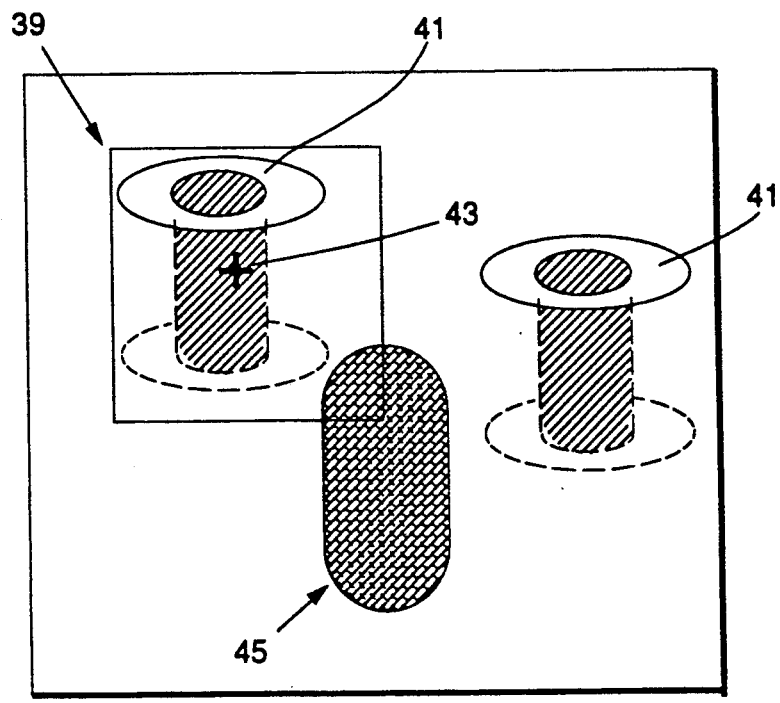
FIG.6
FIG. 7.
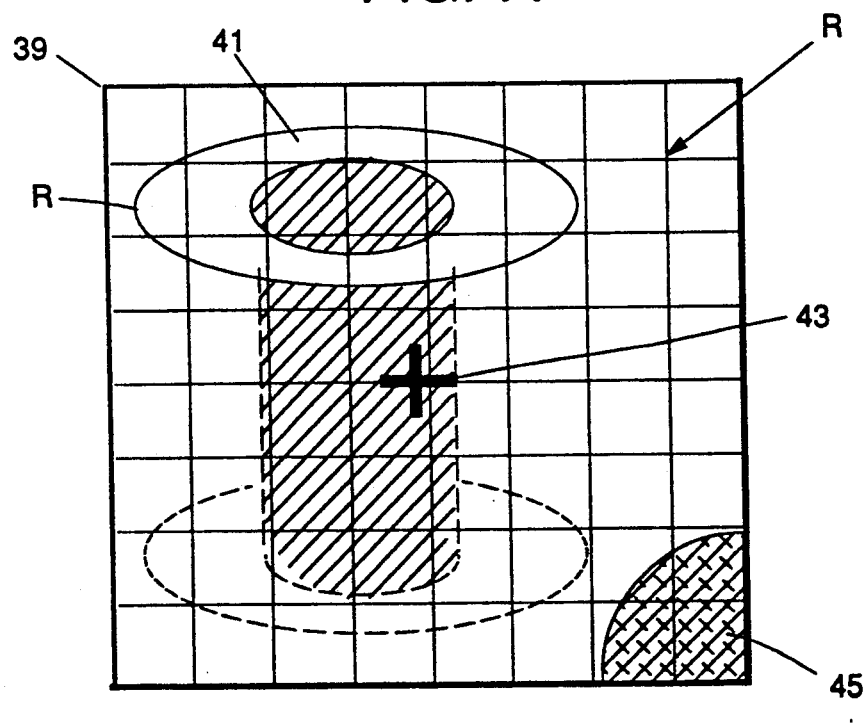

SOLDER JOINT LOCATOR

BACKGROUND OF THE INVENTION

1. Technical Field

This invention relates to systems and methods for analyzing images, and more particularly, to system for locating features in an image.

2. Discussion

One of the primary goals of image processing is to automatically recognize certain features or textures within an image. In typical image processing systems, fields of picture elements (pixels) are automatically scanned, and some algorithm is chosen to analyze the image to recognize particular features. One approach is to arbitrarily select a given region, or window, in the image and to analyze the pixels within the window to detect the particular features. For example, one previous approach is to calculate a centroid, or weighted centroid, on all of the pixels within a window that are below a certain fixed threshold, where the desired feature is known to have an intensity below the threshold. This kind of approach, however, often causes adjacent objects, that are not sought to be detected, to add errors to the calculation when they fall below the threshold. In addition, often such thresholds must be set somewhat higher than desirable to account for variability in the desired features. This higher intensity threshold often can allow for even more errors from adjacent objects. Thus, it would be desirable to provide an image processor which is less prone to detect unwanted features adjacent to the desired features to more accurately analyze the desired features. In addition, it would be desirable to provide an image processor in which the threshold used to detect the features is adaptable to particular portions of the image, and not fixed. In this way the threshold may be set more closely approximate the intensity of the feature.

One image processing application of particular concern, is the task of automatically inspecting printed circuit boards. This task is made more complicated because the mechanical systems employed in the manufacture of printed circuit boards do not always position solder joints in exactly the same place every time. In addition, a the number of features of the board vary from board to board.

An early step in such automatic inspection systems is to analyze an image of the printed circuit board. For example, this may be an X-ray image. As a result of inaccuracies in manufacturing, when an automatic inspection system attempts to inspect a particular feature on the board, such as a solder joint, the physical appearance of the joint in the image does not match from one board to the next, or from one production run to the next. Thus, to accomplish automatic inspection of printed circuit boards, there is needed a way to find the physical position of the joint in an image accurately enough to perform all of the subsequent tests. If the feature, such as the solder joint is not accurately located, the subsequent testing will give faulty results.

For example, if the system is looking for an area that should have substantial amounts of solder but the test system is slightly offset so that it does not look at the center of the solder joint, the system may assume that there should be solder where it should not be and classify a good joint as a bad joint. Conversely, this problem may also cause the system to label a bad joint, a good joint.

Thus, it would be desirable to provide an image processing system which can accurately find the center of features on a printed circuit board, such as solder joints, to improve the accuracy of automatic testing systems.

SUMMARY OF THE INVENTION

Pursuant to the present invention, a method and system is provided for automatically detecting features in an image. The system comprises a means for measuring and storing the intensity of pixels in the image, and a means for defining a window within the image. This window is selected so that the center of the window is coincident with the expected center of the feature to be located. The system also includes a means for determining which pixels in the window are below a predetermined upper threshold of intensity. The system also determines if pixels found below the threshold are connected to the center pixel and labels those pixels as feature pixels. Also, the system determines if pixels found to below the threshold are connected to any pixels previously labeled feature pixels, and labels those pixels also feature pixels. Finally, the system determines the center of the group of feature pixels and displays the coordinate location of this center.

To further improve the ability to recognize desired features, in accordance with a second embodiment of the present invention, there is provided a means for adaptively setting the threshold for each window that is analyzed. This is done by providing a means for measuring the intensity of a solder strip of known thickness in the image. The system then can set a threshold that is equal to this measured intensity of the solder strip. The system further measures the intensity of several pixels in the vicinity of the center pixel and determine the darkest of these pixels. The system then will determine if this darkest pixel is lighter than the previously set threshold. If it is, the system stops because this would mean that the feature falls outside the acceptable range. For example, this could mean a defective solder joint. On the other hand, if the darkest pixel is not lighter than the threshold, then a new threshold is set that is equal to the value of this darkest pixel plus a predefined margin. As a result, the threshold used by the system is adapted for each window to be closely calibrated to the particular intensity of the feature to be analyzed. In this way, there is less likelihood of the system mistakenly identifying a nonfeature as a feature.

BRIEF DESCRIPTION OF THE DRAWINGS

The various advantages of the present invention will become apparent to one skilled in the art, by reading the following specification and by reference to the drawings in which:

FIG. 6 is a perspective view of a PC board including two solder joints, the board being tilted 40° from the vertical.

FIG. 7 is a perspective view of a window in the board of FIG. 6 including a plurality of subwindows.

DESCRIPTION OF THE PREFERRED EMBODIMENT

Figure 1:
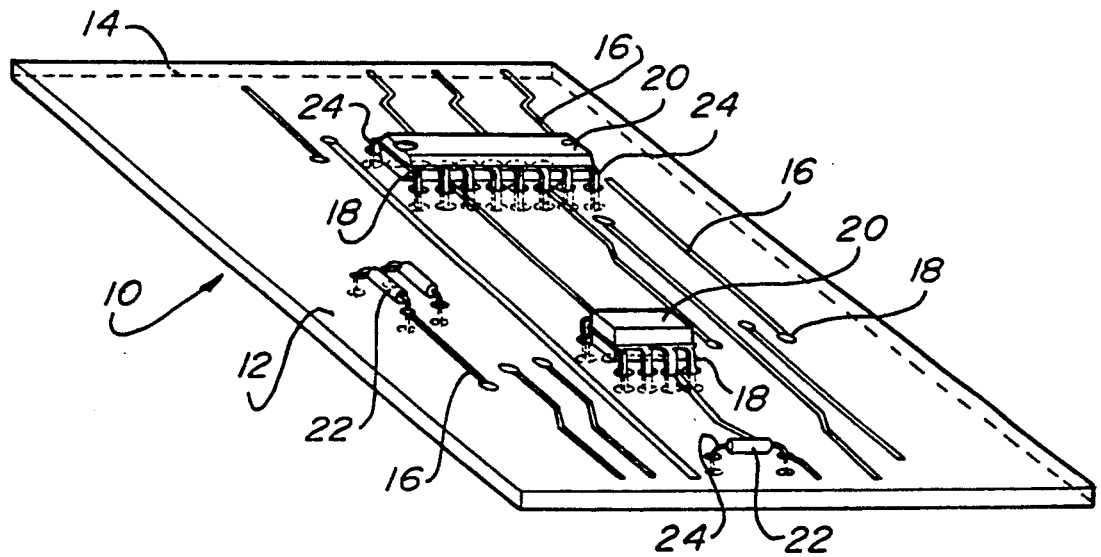
FIG. 1 is a perspective view of a printed circuit board showing portions of the underside in phantom.

The basic approach for locating features in an image according to the present invention, will be illustrated as they are applied to the task of locating solder joints in a PC board for automatic inspection procedures. FIG. 1 illustrates a conventional printed circuit board 10 which is a typical copper clad dielectric material printed wiring board. The circuit board 10 includes a top surface 12 and a bottom surface 14 with conventional conductors 16 etched on both the top and bottom surfaces 12, 14. The printed circuit board 10 includes a number of plated-through holes 18 which provide electrical continuity between the two sides 12, 14. The plated-through holes 18 are created by drilling a hole through the circuit board 10 and the cylindrical surface formed thereby is plated by a chemical deposition process, and then electro-plated to form the interconnections between the top and bottom layers 12 and 14, or for mounting of electronic parts.

Figure 2:
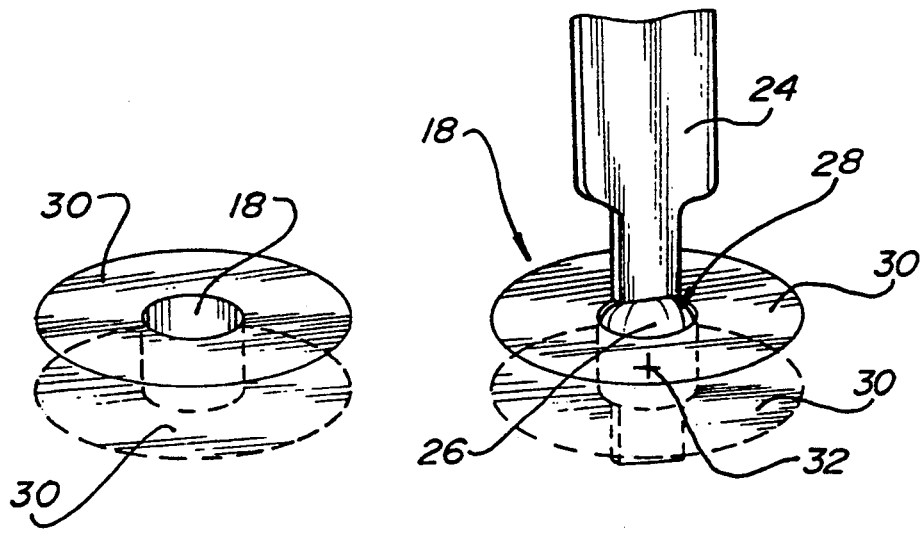
FIG. 2 is a perspective view of a portion of the printed circuit board shown in FIG. 1.

Electrical components may include, for example, integrated circuits 20 or discrete components 22, such as resistors and diodes. These components 20, 22 are generally mounted onto the printed circuit board 10 by placing conductive leads 24 through the plated-through holes 18 so that a portion of the leads 24 extends through the bottom layer 14 of the PC board 10. Next, solder 26 is applied to the plated-through hole 18 and conductive lead 24 to create a solder joint, 28 as best illustrated in FIG. 2. FIG. 2 also illustrates that each solder joint 28 further includes a pair of conductive pads 30 which are in electrical contact with the printed wires 16 and are placed on the top surface 12 as well as the bottom surface 14 of the printed circuit board 10. The solder 26 if properly applied, fills the plated-through hole 18 and adheres to the pad 28 as well as the component lead 24.

In order to insure that printed circuit boards 10 are properly manufactured, a number of automatic testing systems exist. An initial step in many of these testing procedures is to take an X-ray image of the printed circuit board 10 and then to analyze this image for defects that may be apparent in the image. Once this analysis is complete, actual testing of electrical continuity and electrical function of the board may then follow. In such automatic testing systems, one of the first tests is to determine with accuracy, the location of solder joints.

A tilted view X-ray image of a portion of PC board 10 may appear similar to the view in FIG. 2, minus the shading. It will be appreciated that a tilted view is preferable to straight on view since a straight-on, or vertical, view would reveal the top pad and lower pads 30 superimposed on each other and one would not be able to distinguish the two, as is possible with a tilted view.

For automatic analysis of the X-ray image of the PC board 10, it is desired to locate the center of the solder joint, shown by cross 32 in FIG. 2. Cross 32 therefore ideally lies at the theoretical center of the barrel shaped plated-through hole 18. Thus, the present invention provides a system, and method, for determining this theoretical center of the plated-through hole 18 so that subsequent image processing techniques can be used to analyze, in great detail, the integrity of the solder joint 26. In particular, these procedures will look for defects, such as voids in the solder 26, defects in the pad 30, improper placement of the lead 24, empty plated-through holes 18, etc.

In accordance with the present invention, the expected center location 32 is established from known dimensions in the PC board 10 and test X-ray image. The system in accordance with the present invention will then determine with greater accuracy the true location of the center of the hole 32.

Figure 3:
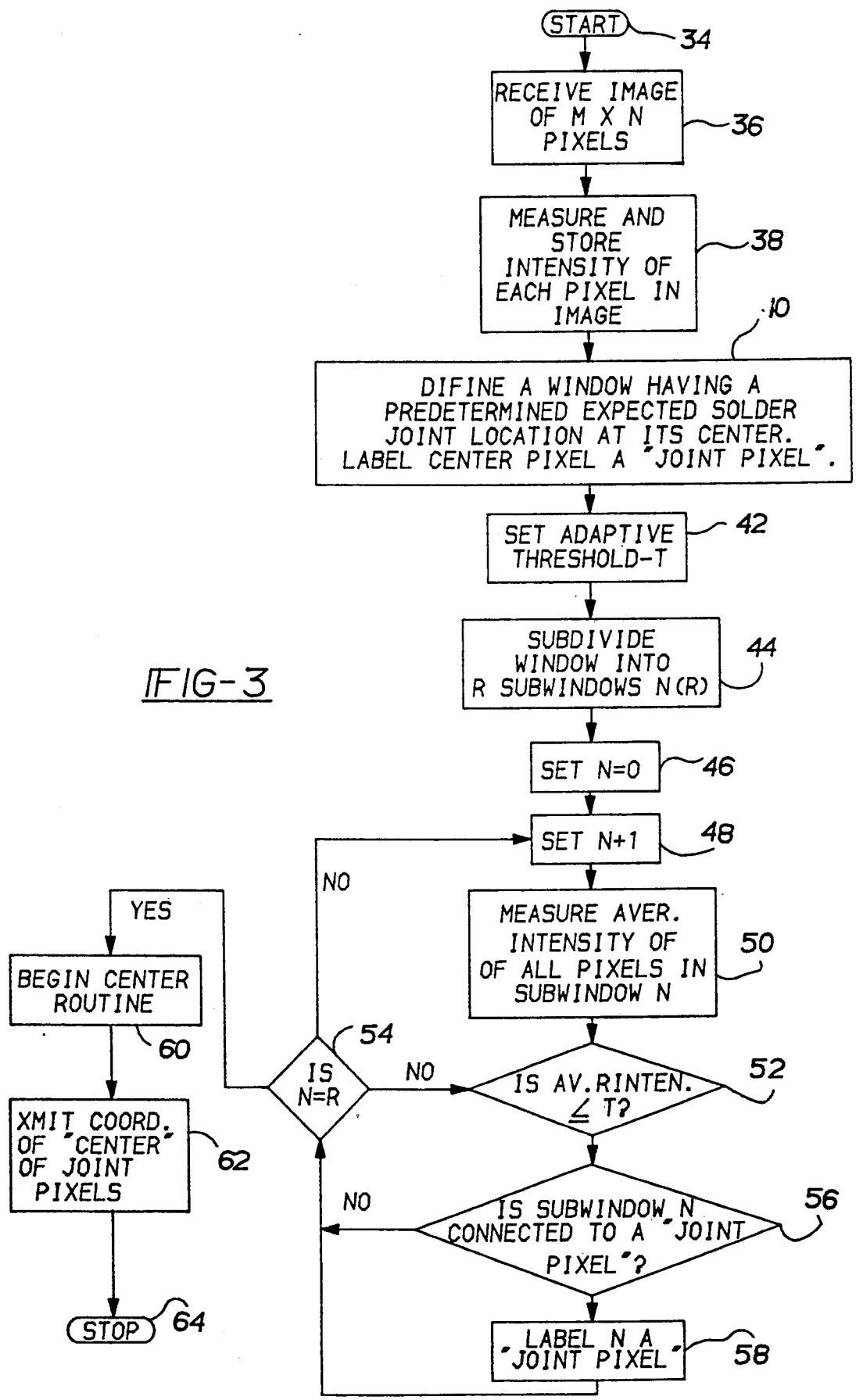
FIG. 3 is a flowchart of the process steps to detect solder joints in performed in accordance with the present invention.

It is assumed that the expected center will be somewhere within the solder joint. If it does not, however, the expected center is so far off that the present invention will probably not be able to find it. For such cases, the present invention will likely detect that something is wrong and will abort the test. See, for example, FIG. 3 and accompanying discussion below.

Figure 4:
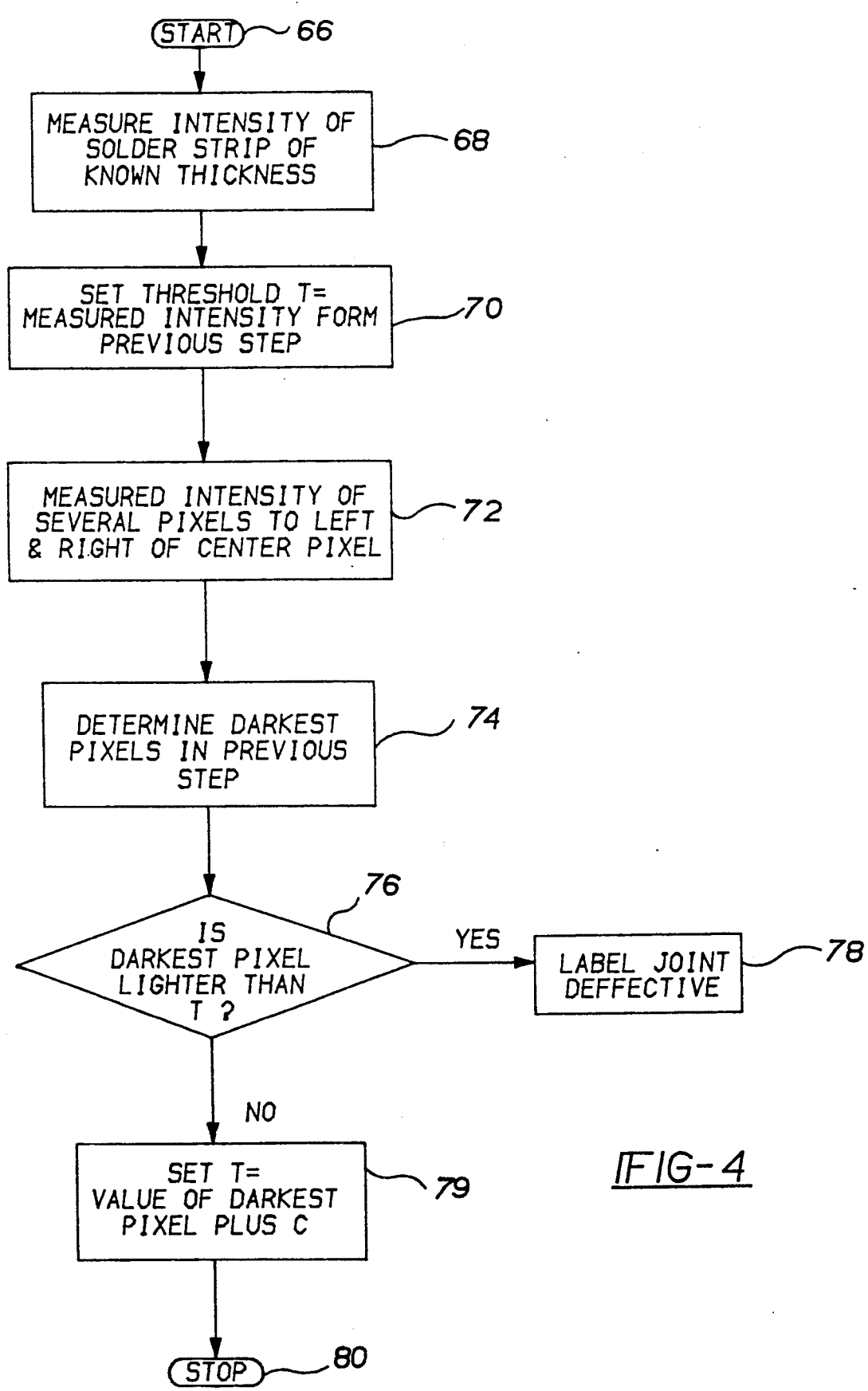
FIG. 4 is a flowchart showing the process steps to set the adaptive threshold in accordance with the present invention.

Referring now to FIGS. 4, 6 and 7, a method, in accordance with the present invention, for finding the center 32 of a solder joint, will now be described. In block 34 the processing begins. In the first step 36 the tilted view X-ray image 37 of the PC board is received. This image will comprise discrete pixels; in general, the image will contain m x n pixels. Next, the intensity of each pixel is measured and this intensity value is stored. (step 38) Next, a "window" 39 is defined such that a predetermined expected solder joint location 41 is at its center. This center pixel 43 is labeled a "joint pixel". (step 40) An object 45 other than a solder joint 41 as shown in window 39 for purposes of comparison.

It will be appreciated that there will be a desired location for the solder joint in the PC board and that this known location can be coordinated with a given pixel in the image. For example, solder joint locations can be assigned x-y coordinate locations, and the PC board image can then be related to these coordinate locations to determine which pixel in the image is expected to be at the center of each solder joint location.

The upper intensity threshold T is then set. (step 42) This may be preferably an adaptive threshold which is set in accordance with the process described below in connection with FIG. 4. However, a nonadaptive threshold could be set which would simply be an estimated upper limit of the possible intensity value for a joint pixel. Next, the window 39 is subdivided into R subwindows. (step 44) This step speeds up the processing by analyzing groups of pixels rather than each pixel individually. However, it will be appreciated that individual pixels could be analyzed, and in some applications it may be desirable to do so depending on the desired resolution and speed of processing.

In accordance with a preferred embodiment, the subwindows consist of a square area within the window of nine pixels having a single pixel at its center. Next, each subwindow is analyzed individually until the entire window has been processed. It may be accomplished by assigning each subwindow an index number N from one to R. This index is first set to zero (step 46) and is then incremented by one each time step 48 is carried out. Next, the average intensity of all the pixels in the subwindow N is measured. (step 50) Then, the average intensity of the subwindow is compared to the upper threshold T in step 52. If this average intensity is not less than or equal to T, then the subwindow is considered to be not part of the solder joint and the process proceeds to step 54 to determine if there are any further subwindows that have not yet been processed. If there are, that is, if N is not equal to R, step 54 directs the process back to step 48 to proceed to the next numerically consecutive subwindow.

If, on the other hand, step 52 determines that the average intensity is less than or equal to T, step 56 is performed, which determines whether the subwindow N is "connected" to any "joint pixels". It will be appreciated that a number of different criteria could be used to determine if pixels are "connected." Preferably this criteria will require more than a single side to be connected, or touching. This will avoid the connection of two separate features by a thin string of pixels. For example, the criteria preferred is that three sides touch to establish connectedness. It should also be noted that in step 40, the center pixel was labeled a joint pixel, and that the processing will proceed on subwindows that are "connected" to the center pixel and proceed outward until all of the subwindows in the window have been analyzed. If, in step 56 it is determined that the subwindow N, which had its intensity less than or equal to T, is not connected a "joint pixel", then that subwindow is considered to be not part of the joint. For example, this may represent a dark area corresponding to an electrical component that is not part of the particular solder joint. Alternatively, it may represent a completely different solder joint that is within the window. It should be noted that the other solder joints will be ignored at this point, but will be processed at a later time when a different window is selected having the expected center joint of that solder joint at its center.

Accordingly, step 56, having determined that a window is not connected to a joint window, will direct the system to step 54, where, as described above, it will be determined whether there are additional subwindows to analyze. If there are, the process will proceed to step 48. If, on the other hand, step 56 determines that the subwindow is connected to a joint pixel, then the pixels in that subwindow is labeled a "joint pixels". (step 58) It will be appreciated that subwindows with pixels labeled "joint pixels", may be connected to the center pixel, or may it be connected to other subwindows previously determined to be connected to the center window, or to other subwindows labeled "joint pixels".

After 58, step 54 is again performed to determined if there are additional subwindows not yet processed. If there are not, that is, if N is equal to R, then step 60 is performed to begin a centering routine. That is, the above steps will have determined all subwindows that are connected to each other and below or equal to threshold T and labeled those pixels joint pixels. The subwindows at this point, should define the generally cylindrical or barrel shape of the solder joint 28. It will be appreciated that given this cylindrical shape, one can easily determine the center of this shape. For example, a procedure may employ averaging techniques whereby the average location is determined. In particular, such a centering technique may proceed as follows. Initially, each subwindow is assigned an X-Y value, corresponding to the center of the subwindow. The X, Y value of all "joint" subwindows are then averaged separately to given an overall joint X, Y. Optionally, additional procedures may be performed to check the shape of the group of joint pixels before the centering routine is begun. For example, in accordance with conventional image processing techniques, the joint pixels may be analyzed to see if they generally form a rectangular shape.

Having found the center of the solder joint, 41 the coordinates of the center pixel 43 are now determined and are transmitted for display, or for use by subsequent processing systems (Step 62). At this point the processing, is complete (step 64). All of the above steps, 34-64, may be repeated for other solder joints 28 in the PC board 10. Alternatively, different features besides solder joints, may be analyzed in accordance with the above steps.

Referring now to FIG. 4, the preferred method for setting an adaptive threshold, in accordance with step 42 above, will now be described. The procedure for setting the adaptive threshold begins with the measurement of the intensity of a calibration strip of the solder on the PC board 10. (steps 66 and 68). This calibration strip is preferably contained within the window defined in step 40 of FIG. 3. This is because the threshold is reset for each window. Alternatively, since the adaptive threshold also depends on the intensity in the neighborhood of the center pixel, there could be only a single calibration strip in the entire PC board, in which case the measurement taken in step 68 is used for each window in the entire image.

The threshold is initially set to be the intensity of the solder strip measured in step 68 (step 70). This is because the calibration strip, measured in step 68, is chosen to yield an intensity value that would represent the lightest acceptable value for a solder joint area. Next, measurements are taken of the intensity of several pixels in the neighborhood of the center pixel defined in step 40. (step 72) Next, the darkest of these pixels is selected (step 74). The darkest pixel is then compared to the threshold set in step 70. (step 76) If this darkest pixel is lighter than the threshold, the joint is labeled defective. (step 78). This is because the calibration solder strip is as light as a solder joint should be. If it is lighter there is a problem, such as a void in the joint, and the joint is labeled defective and the processing stops as shown in step 78. On the other hand, if the darkest pixel is not found to be lighter in step 76, the threshold is set to a new value which is equal to the darkest pixel plus some predefined constant value, C. (steps 79 and 80).

Figure 5:
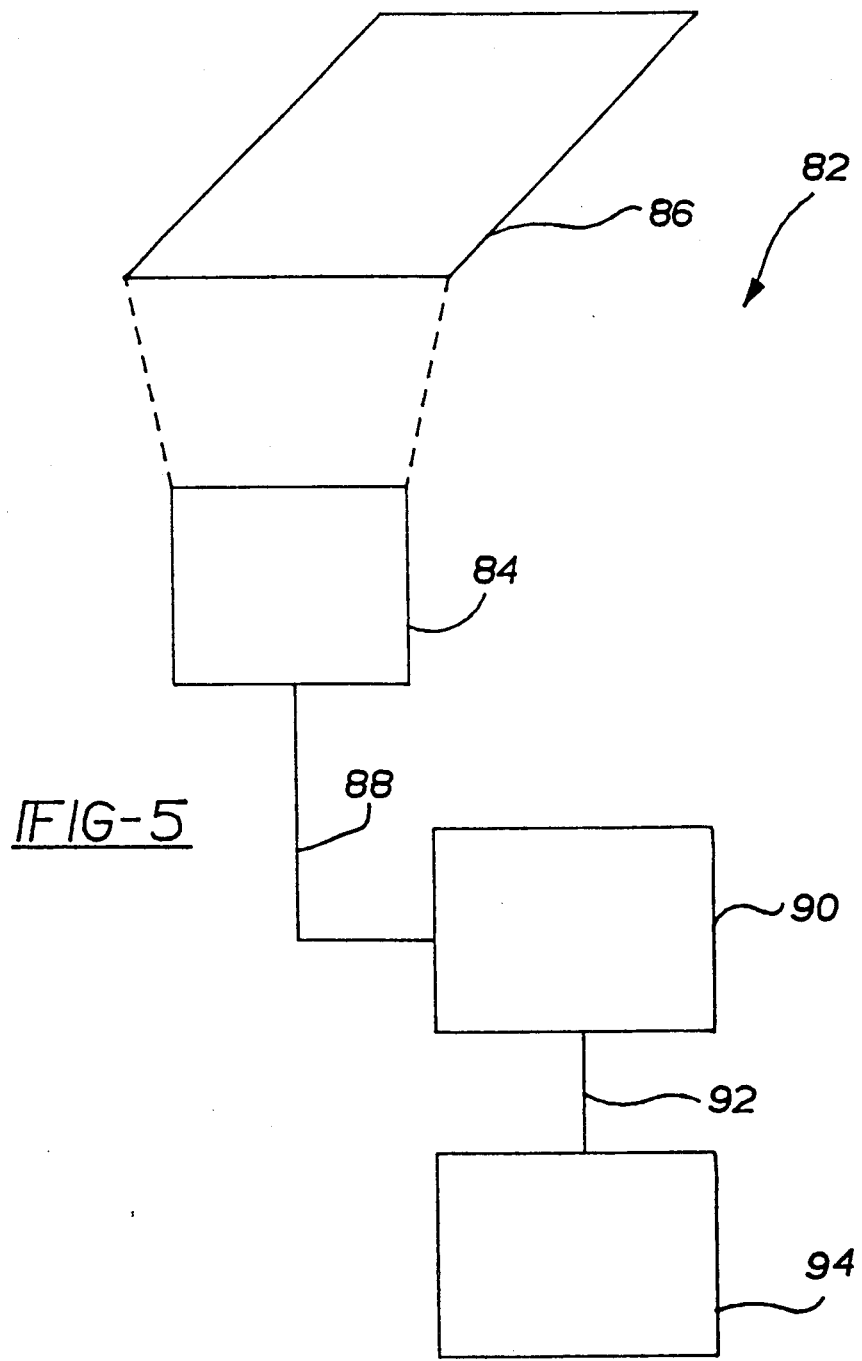
FIG. 5 is a block diagram of a microprocessor controlled version of one embodiment of the present invention.

Referring now to FIG. 5, a preferred embodiment of the hardware according to the present invention is shown. A solder joint locator system 82 includes a sensor 84 which may comprise, for example, a CCD array for detecting the intensity of the individual pixels in an image, such as an X-ray image 86 of a PC board. The information from the CCD array is fed along bus 88 to a microcontroller 90. Microcontroller 90 comprises a conventional programmable microprocessor capable of receiving the pixel data from CCD array 84 and storing and processing this information. In particular, microcontroller 90 is programmed to perform all of the steps 34 through 64 in FIG. 3, as well as the adaptive threshold setting steps 66-80 in FIG. 4. Finally, microcontroller 90 is connected, by means of bus 92, to a postprocessing system 94 which uses the coordinate locations of the solder joint centers found by the microcontroller 90 to perform additional tests on the PC board image 86. In addition, direct tests to the actual PC board may then also be performed.

It will be appreciated that in some circumstances desired features will be lighter rather than darker than the background. In such cases, the invention will be adapted to set lower thresholds and to look for pixels that are lighter than the lower thresholds. Alternatively, an intensity band, rather than an upper or lower threshold, may be set. In which case the invention may be adapted to look for pixels that fall within this band. It should also be recognized that the joint locator system 82 and the processes described in FIGS. 3 and 4, can also be employed in other image processing applications besides locating joints in PC boards. For instance, the present invention could be used in target acquisition where, for example, the image is an infrared image and the image processing task is tracking of bright spots in the image. The present invention could then be used to sort out and track separate spots in such an image. In general, the present invention can be used in a wide variety of image processing applications where the center of an object in a field is desired and the field is cluttered with other things that will obscure the task of finding the center of the object. While the above description constitutes the preferred embodiments of the present invention, it will be appreciated that the invention is susceptible to modifications, variation and change without departing from the proper scope and fair meaning of the accompanying claims.

What is claimed is:

1. A system for automatically detecting features in an image, said system comprising:
   means for measuring the intensity of pixels in said image, each pixel having a coordinate location;
   means for storing said measured intensity valves;
   means for defining a window within said image, the window having one of said predetermined expected feature locations at its center pixel;
   means for labeling the center pixel;
   means for determining if the intensity of pixels within said window are below a predetermined upper threshold;
   means for determining if pixels found to be below said predetermined upper threshold are connected to the center pixel, and for labeling those pixels;
   means for determining if pixels found to be below the predetermined upper threshold are connected to any pixels previously labeled, and for labeling those pixels also;
   means for determining the center of the group of labeled pixels; and
   means for displaying the coordinate location of said center.

2. The system of claim 1 further comprising:
   means for determining said upper threshold comprising means for measuring the intensity of a calibration portion of said image;
   means for determining the darkest pixel in the neighborhood of the center pixel;
   means for comparing said darkest pixel with the calibration portion; and
   means for setting the upper threshold equal to said darkest pixel plus a predetermined constant if it is darker than the calibration portion.

3. The system of claim 2 wherein said means for determining the upper threshold further comprises means for identifying the feature if said darkest pixel is lighter than the calibration portion.

4. The system of claim 1 wherein said image is a tilted view X-ray image of a printed circuit board.

5. The system of claim 4 wherein said feature is a solder joint in a plated-through hole in said printed circuit board.

6. A system for automatically determining the position of features in an image, said system comprising:
   means for measuring the intensity of pixels in said image, said pixels having coordinate locations in said image;
   means for storing said measured intensity values;
   means for defining a window within said image having a predetermined expected feature location at its center pixel;
   means for dividing said window into a plurality of sub-windows;
   means for labeling the pixels in the sub-window surrounding the center of the window as feature pixels;
   means for determining the average intensity of pixels within each of said sub-windows;
   means for determining if the average intensity of pixels within each sub-window are below a predetermined upper threshold;
   means for determining if pixels in sub-windows found to be below said predetermined upper threshold are connected to feature pixels and for labeling those as feature pixels;
   means for determining if pixels in sub-windows found to be below the predetermined upper threshold are connected to any pixels previously labeled feature pixels, and labeling those pixels also as feature pixels;
   means for determining the center of the group of the feature pixels; and
   means for displaying the coordinate location of said center.

7. The system of claim 6 further comprising:
   means for determining said upper threshold comprising means for measuring the intensity of a calibration portion of said image;
   means for determining the darkest pixel in the neighborhood of the center pixel;
   means for comparing said darkest pixel with the calibration portion; and
   means for setting the upper threshold equal to said darkest pixel plus a predetermined constant if it is darker than the calibration portion.

8. The system of claim 7 wherein said means for determining the upper threshold further comprises means for identifying the feature if said darkest pixel is lighter than the calibration portion.

9. The system of claim 6 wherein said image is a tilted view X-ray image of a printed circuit board.

10. The system of claim 9 wherein said feature is a solder joint in a plated-through hole in said printed circuit board.

11. A system for testing printed circuit boards for solder joint locations by analyzing an X-ray image of the printed circuit board, said system comprising:
    means for measuring the intensity of pixels in said image, said pixels having coordinate locations in said image;
    means for storing said measured intensity valves;
    means for defining a window within said image having a predetermined expected joint location at its center pixel;
    means for dividing said window into a plurality of sub-windows;
    means for labeling the pixels in the sub-window surrounding the center of the window as joint pixels;
    means for determining the average intensity of pixels within each of said sub-windows;

means for determining if the average intensity of pixels within each sub-window are below a predetermined upper threshold;

means for determining if pixels in sub-windows found to be below said predetermined upper threshold are connected to joint pixels and for labeling those joint pixels;

means for determining if pixels in subs-windows found to be below the predetermined upper threshold are connected to any pixels previously labeled feature pixels, and labeling those pixels also joint pixels;

means for determining the center of the group of the joint pixels; and means for displaying the coordinate location of said center.

12. The system of claim 11 further comprising:

means for determining said upper threshold further comprising means for measuring the intensity of a calibration portion of said image;

means for determining the darkest pixel in the neighborhood of the center pixel;

means for comparing said darkest pixel with the calibration portion; and means for setting the upper threshold equal to said darkest pixel plus a predetermined constant if it is darker than the calibration portion.

13. A method for automatically determining the position of features in an image, said method comprising the steps of:

measuring the intensity of pixels in said image, said pixels having coordinate locations in said image;

storing said measured intensity values;

defining a window within said image having a predetermined expected feature location at its center pixel;

dividing said window into a plurality of sub-windows;

labeling the pixels in the sub-window surrounding the center of the window as feature pixels;

determining the average intensity of pixels within each of said sub-windows;

determining if the average intensity of pixels within each sub-window are below a predetermined upper threshold;

determining if pixels in sub-window found to be below said predetermined upper threshold are connected to feature pixels and for labeling those as feature pixels;

determining if pixels in sub-windows found to be below the predetermined threshold are connected to any pixels previously labeled feature pixels, and labeling those pixels also as feature pixels;

determining the center of the group of the feature pixels; and displaying the coordinate location of said center.

14. The system of claim 13 further comprising:

determining said upper threshold comprising means for measuring the intensity of a calibration portion of said image;

determining the darkest pixel in the neighborhood of the center pixel;

comparing said darkest pixel with the calibration portion; and setting the upper threshold equal to said darkest pixel plus a predetermined constant if it is darker than the calibration portion.

15. The system of claim 13 wherein determining the upper threshold further comprises stopping the system and identifying the feature if said darkest pixel is lighter than the calibration portion.

16. A method for automatically testing a printed circuit board to determine the position of solder joints in a tilted view X-ray image of the printed circuit joint or circuit board, said method comprising:

measuring the intensity of pixels in said image, said pixels having coordinate locations in said image;

storing said measured intensity values;

defining a window within said image having a predetermined expected joint location at its center pixel;

dividing said window into a plurality of sub-windows;

labeling the pixels in the sub-window surrounding the center of the window as joint pixels;

determining the average intensity of pixels within each of said sub-windows;

determining if the average intensity of pixels within each sub-window are below a predetermined upper threshold;

determining if pixels in sub-windows found to be below said upper threshold are connected to joint pixels and for labeling those joint pixels;

determining if pixels in subs-windows found to be below the threshold are connected to any pixels previously labeled feature pixels, and labeling those pixels also joint pixels;

determining the center of the group of the joint pixels; and displaying the coordinate location of said center.

* * * * *